(12) United States Patent
Firat et al.

(10) Patent No.: US 7,345,026 B2
(45) Date of Patent: Mar. 18, 2008

(54) HYBRID OR CHIMERIC POLYNUCLEOTIDES, PROTEINS, AND COMPOSITIONS COMPRISING HEPATITIS B VIRUS SEQUENCES

(75) Inventors: Hüseyin Firat, Paris (FR); François Lemonnier, Bourg-la-Reine (FR); Pierre Langlade-Demoyen, Paris (FR); Marie-Louise Michel, Paris (FR); Andreas A. Suhrbier, Bunya (AU)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 10/388,337

(22) Filed: Mar. 14, 2003

(65) Prior Publication Data

US 2004/0018208 A1    Jan. 29, 2004

Related U.S. Application Data

(63) Continuation of application No. 09/671,198, filed on Sep. 28, 2000, now abandoned.

(60) Provisional application No. 60/156,945, filed on Sep. 30, 1999.

(51) Int. Cl.
*A61K 35/00* (2006.01)
*C12N 15/68* (2006.01)

(52) U.S. Cl. .................... 514/44; 435/320.1
(58) Field of Classification Search ............... 536/23.4, 536/23.7, 23.72, 189.1, 192.1; 424/189.1, 424/192.1, 199.1, 227.1; 514/44; 435/320.1
See application file for complete search history.

(56) References Cited

U.S. PATENT DOCUMENTS

| | | | |
|---|---|---|---|
| 4,722,840 A | 2/1988 | Valenzuela et al. | |
| 5,662,907 A | 9/1997 | Kubo et al. | |
| 5,792,463 A | 8/1998 | Valenzuela et al. | |
| 5,844,075 A | * 12/1998 | Kawakami et al. | 530/326 |
| 6,133,244 A | * 10/2000 | Michel et al. | 514/44 |

FOREIGN PATENT DOCUMENTS

| | | | |
|---|---|---|---|
| WO | WO 95/22317 A1 | * | 8/1995 |
| WO | WO9741440 A1 | * | 11/1997 |
| WO | WO 99/46392 | | 9/1999 |
| WO | WO 00/04149 | | 1/2000 |

OTHER PUBLICATIONS

Melegari et al. J. Virol. 1997, vol. 71, No. 7, pp. 5449-5454.*
Shouval et al. Proc. Natl. Acad. Sci. USA, 1988, vol. 85, pp. 8276-8280.*
Chen et al. Proc. Natl. Acad. Sci. 1996, vol. 93, pp. 1997-2001.*
Conry et al. Clin. Caner Res. 1998, vol. 4, pp. 2903-2912.*
Michel et al. Proc. Natl. Acad. Sci. USA, 1995, vol. 92, pp. 5307-5311. (A).*
Michel et al. Proc. Natl. Acad. Sci. USA, 1988, vol. 85, pp. 7957-7961. (B).*
Le Borgne et al. Virol. 1998, vol. 240, pp. 304-315.*
Bryder et al. (DNA and Cell Biology, Mar. 1999, vol. 18, No. 3, pp. 219-225.*
Toes et al. Proc. Natl. Acad. Sci. USA, 1997, vol. 94, pp. 14660-14665.*
Schirmbeck et al. Eur. J. Immunol. 1999, vol. 29, pp. 1740-1749.*
Schell et al. Cancer Research 2000, Viol. 61, pp. 873-879.*
Arnold, B., et al., "MHC Class-1 Transgenic Mice", *Ann. Rev. Immunol.* 9:297-322, 1991.
Bednarek, M.A., "The Minimum Peptide Epitope from the Influenza Virus Matrix Protein. Extra and Intracellular Loading of HLA-A2", *J. Immunol.* 147(12):4047-4053, Dec. 15, 1991.
Burns, N.R., et al., "Production and Purification of Hybrid Ty-VLPs", *Mol. Biotechnol.* 1(2):137-145, Apr. 1994.
Deres, K., et al., "In Vivo Priming of Virus-Specific Cytotoxic T Lymphocytes with Synthetic Lipopeptide Vaccine", *Nature* 342(6249):561-564, Nov. 30, 1989.
Falk, K., et al., "Allele-Specific Motifs Revealed by Sequencing of Self Peptides Eluted from MHC Molecules", *Nature* 351(6324):290-296, May 23, 1991.
Gao, G.F., et al., "Crystal Structure of the Complex Between Human CD8alpha(alpha) and HLA-A2", *Nature* 387:630-634, Jun. 5, 1997.
Hagen et al. *P.N.A.S.*, 91:12808-12812, 1994.
Huang, A.Y., et al., "Role of Bone Marrow-Derived Cells in Presenting MHC Class I-Restricted Tumor Antigens", *Science* 264:961-965, May 13, 1994.
Inaba, K., et al., "Granulocytes, Macrophages, and Dendritic Cells Arise from a Common Major Histocompatability Complex Class II-Negative Progenitor in Mouse Bone Marrow", *Proc. Natl. Acad. Sci. USA* 90(7):3038-3042, Apr. 1, 1993.
Jakubezak et al. *Cancer Res.*, 57:3606-3611, 1997.
Kalinke, U., et al., "Strong Xenogeneic H.A. Response in Transgenic Mice After Introducing an α3 Domain into H.A.-B27", *Nature* 348(6302):642-644, Dec. 13, 1990.

(Continued)

*Primary Examiner*—Bruce R. Campell
*Assistant Examiner*—Bao Qun Li
(74) *Attorney, Agent, or Firm*—Finnegan, Henderson, Farabow, Garrett & Dunner, LLP

(57) ABSTRACT

H-2 class I negative, HLA-A2.1 transgeniic HHD mice were used for a comparative evaluation of the immunogenicity of HLA-A2.1 restricted human tumor-associated CTL epitopes. A hierarchy was established among these epitopic peptides injected into mice in IFA which correlates globally with their capacity to bind and stabilize HLA-A2.1 molecules. Co-injection of a helper peptide enhanced most CTL responses. In contrast, classical HLA class I transgenic mice which still express their own class I molecules did not, in most cases, develop H.A.-A2.1-restricted CTL responses under the same experimental conditions. Different monoepitopic immunization strategies of acceptable clinical usage were compared in HHD mice. Recombinant Ty-virus-like particles, or DNA encoding epitopes fused to the hepatitis B virus middle envelope protein gave the best results. Using this latter approach and a melanoma-based polyepitope construct, CTL responses against five distinct epitopes could be elicited simultaneously in a single animal. Thus, HHD mice provide a versatile animal model for preclinical evaluation of peptide-based cancer immunotherapy.

7 Claims, 3 Drawing Sheets

OTHER PUBLICATIONS

Kawakami, Y. and Rosenberg, S.A., "Human Tumor Antigens Recognized by T-Cells", *Immunol. Res.* 16(4):313-339, Nov. 1997.

Layton, G.T., et al., "Introduction of Single and Dual Cytotoxic T-Lymphocyte Responses to Viral Proteins in Mice Using Recombinant Hybrid Ty-Virus-Like Particles", *Immunology* 87(2):171-178, Feb. 1996.

Le Borgne, S., et al., "In Vivo Induction of Specific Cytotoxic T Lymphocytes in Mice and Rhesus Macaques Immunized with DNA Vector Encoding an HIV Epitope Fused with Hepatitis B Surface Antigen", *Virology* 240(2):304-315, Jan. 20, 1998.

Mayordomo, J.L., et al., "Bone Marrow-Derived Dendritic Cells Pulsed with Synthetic Tumour Peptides Elicit Protective and Therapeutic Antitumour Immunity", *Nature Med.* 1(12):1297-1302, Dec. 1995.

Melief, C. J., "Tumor Eradication by Adoptive Transfer of Cytotoxic T Lymphocytes", *Adv. Cancer Res.* 58:143-175, 1992.

Michel et al. *P.N.A.S.* 92:5307-5311, 1995.

Milich, D.R., et al., "Hepatitis B Synthetic Immunogen Comprised of Nucleocapsid T-Cell Sites and an Envelope B-Cell Epitope", *Proc. Natl. Acad. Sci. USA* 85(5):1610-1614, Mar. 1988.

Momburg, F., et al., "Selectivity of MHC-Encoded Peptide Transporters from Human, Mouse and Rat", *Nature* 367(6464):648-651, Feb. 17, 1994.

Ossendorp, F., et al., "Specific T Helper Cell Requirement for Optimal Induction of Cytotoxic T Lymphocytes Against Major Histocompatibility Complex Class II Negative Tumors", *J. Exp. Med.* 187(5):693-702, Mar. 2, 1998.

Pascolo, S., et al., "H.A.-A2.1-Restricted Education and Cytolytic Activity of $CD8^+$ T Lymphocytes from $\beta 2$ Microglobulin ($\beta 2m$) H.A.-A2.1 Monochain Transgenic $H-2D^b$ $\beta 2m$ Double Knockout Mice", *J. Exp. Med.* 185(12):2043-2051, Jun. 16, 1997.

PCT Search Report; PCT/EP 00/09900.

Porgador, A., et al., "Induction of Antitumor Immunity Using Bone Marrow-Generated Dendritic Cells", *J. Immunol.* 156(8):2918-2926, Apr. 15, 1996.

Rosenberg, S.A., et al., "Immunologic and Therapeutic Evaluation of a Synthetic Peptide Vaccine for the Treatment of Patients with Metastatic Melanoma", *Nature Med.* 4(3):321-327, Mar. 1998.

Sette, A., et al., "The Relationship Between Class I Binding Affinity and Immunogenicity of Potential Cytotoxic T Cell Epitopes", *J. Immunol.* 153(12):5586-5592, Dec. 1994.

Shirai, M., et al., "CTL Responses of H.A.-A2.1-Transgenic Mice Specific for Hepatitis C Viral Peptides Predict Epitopes for CTL of Humans Carrying H.A.-A2.1", *J. Immunol.* 154(6):2733-2742, Mar. 15, 1995.

Song, W., et al., "Dendritic Cells Genetically Modified with an Adenovirus Vector Encoding the cDNA for a Model Antigen Induce Protective and Therapeutic Antitumor Immunity", *J. Exp. Med.* 186(8):1247-1256, Oct. 20, 1997.

Specht, J.M., et al., "Dendritic Cells Retrovirally Transduced with a Model Antigen Gene Are Therapeutically Effective Against Established Pulmonary Metastases", *J. Exp. Med.* 186(8):1213-1221, Oct. 20, 1997.

Stoute et al., "A Preliminary Evaluation of a Recombinant Circumsporozoite Protein Vaccine Against *Plasmodium Falciparum* Malaria", *The New England Journal of Medicine*, 336(2);86-91, Jan. 1997.

Thomson, S.A., et al., "Delivery of Multiple CD8 Cytotoxic T Cell Epitopes by DNA Vaccination", *J. Immunol.* 160(4):1717-1723, Feb. 15, 1998.

Tsomides, T.J., et al., "An Optimal Viral Peptide Recognized by $CD8^+$ T Cells Binds Very Tightly to the Restricting Class I Major Histocompatibility Complex Protein on Intact Cells But Not to the Purified Class I Protein", *Proc. Natl. Acad. Sci. USA* 88(24):11276-11280, Dec. 15, 1991.

van der Bruggen, P., et al., "A Gene Encoding an Antigen Recognized by Cytolytic T Lymphocytes on a Human Melanoma", *Science* 254:1643-1647, Dec. 13, 1991.

van der Burg, S.H., et al., "Immunogenicity of Peptides Bound to MHC Class I Molecules Depends on the MHC-Peptide Complex Stability", *J. Immunol.* 156(9):3308-3314, May 1, 1996.

Vasilakos, J.P. and Michael, J.G., "Herpes Simplex Virus Class I-Restricted Peptide Induces Cytotoxic T Lymphocytes *in Vivo* Independent of CD4+ T Cells", *J. Immunol.* 150(6):2346-2355, Mar. 15, 1993.

Vitiello, A., et al., "Analysis of the HLA-Restricted Influenza-Specific Cytotoxic T Lymphocyte Response in Transgenic Mice Carrying a Chimeric Human-Mouse Class I Major Histocompatibility Complex", *J. Exp. Med.* 173:1007-1015, Apr. 1991.

Wentworth, P.A., et al., "Differences and Similarities in the A2.1-Restricted Cytotoxic T Cell Repertoire in Humans and Human Leukocyte Antigen-Transgenic Mice", *Eur. J. Immunol.* 26(1):97-101, Jan. 1996.

Wilson, R.K., et al., "Structure, Organization and Polymorphism of Murine and Human T-Cell Receptor Alpha and Beta Chain Gene Families", *Immunol. Rev.* 101:149-172, 1988.

\* cited by examiner

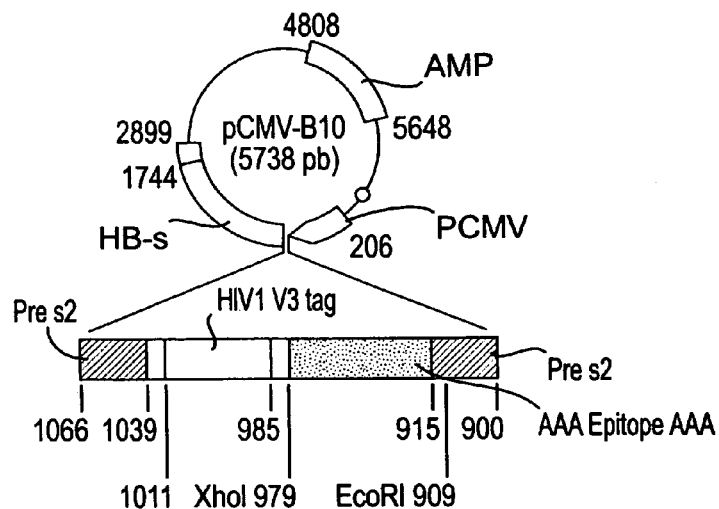
FIG. 1A
AAGIGILTV<u>FLWGPRALV</u>MELAVLYC<u>LLLDGTATL</u>RLKTWGQYWQV
<u>YMDGTMSDV</u>ITDQVPFSVYLEFGPVTAILTVILG<u>VLVLPDVFIRCV</u>
FIG. 1B
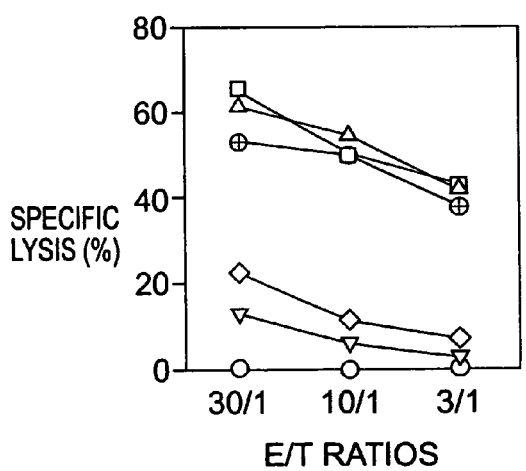
FIG. 1C
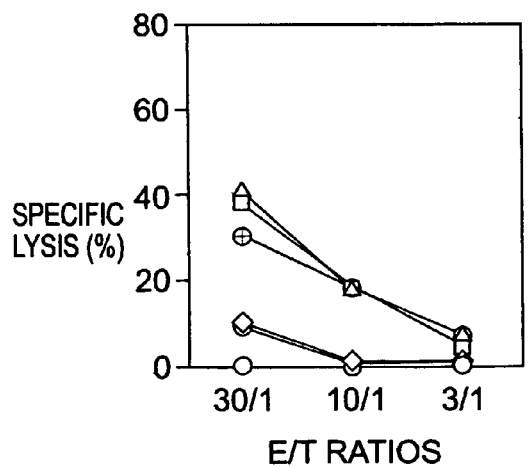
FIG. 1D

HYBRID OR CHIMERIC POLYNUCLEOTIDES, PROTEINS, AND COMPOSITIONS COMPRISING HEPATITIS B VIRUS SEQUENCES

CROSS-REFERENCE TO RELATED APPLICATION

This is a continuation of application Ser. No. 09/671,198, filed Sep. 28, 2000 now abandoned, which claims the right to priority based on Provisional Patent Application No. 60/156,945 filed Sep. 30, 1999. The entire disclosures of both of the priority documents is incorporated herein by reference.

BACKGROUND OF THE INVENTION

1. Field of the Invention

This invention relates to polynucleotides and vectors, to compositions containing the polynucleotides and vectors, to polypeptides and polypeptide compositions, and to their use.

2. Description of Related Art

CTL-mediated protection against tumors has been documented in mouse experimental models (1). In view of our refined comprehension of the molecular structures recognized by CTL, the search for human tumor-derived CTL epitopes has been undertaken in many laboratories, as best exemplified for melanomas (2). Subsequently, clinical trials using peptide-based immunization protocols provided encouraging results (3). However, the selection of peptide(s) and vaccine strategy remain difficult in view of the number of candidate peptides and variety of immunization strategies. An animal model allowing a controlled evaluation of the immunogenic potential of the epitopic peptides and of the immunization strategies would be of interest before human immunotherapeutic trials.

Classical H.A. class I transgenic mice (which still express their own H-2 class I Classical H.A. class I transgenic mice (which still express their own H-2 class I molecules) have been derived for such purposes (4). However, unless the third domain of the human molecules was substituted with the corresponding mouse domain, the peripheral CTL repertoire of these mice was inefficiently mobilized by the transgenic molecules due to poor interaction with mouse CD8 molecules (5). Accordingly, improved usage of H.A. class I molecules has been documented in transgenic strains expressing chimeric constructs (α1, α2 human, and α3 mouse) and exploited for the study of CTL responses against certain viral and tumor epitopic peptides (6, 7). Nevertheless, in such mice we observed a profound bias in favor of H-2 restricted CTL responses (H. Firat, unpublished observations). To circumvent that bias, we derived a strain of mice in which the H-2 $D^b$ and mouse b2-microglobulin (β2m) genes have been disrupted and which expresses a chimeric (α1, α2 human, and α3 mouse) HLA-A2.1 heavy chain covalently linked to human b2m light chain. We named this chimeric molecule the HHD molecule. In HHD transgenic mice, the transgenic molecules are the only class I molecules serologically detectable on cell surfaces and are used efficiently by CTL in responses against viruses (8). We report here the use of these mice to compare the immunogenic potential of H.A.-A2.1-restricted human tumor-associated CTL epitopes and different strategies of immunization.

SUMMARY OF THE INVENTION

Accordingly, this invention provides polynucleotides containing at least part of the coding sequence of the middle glycoprotein of the hepatitis B virus in which is inserted a DNA sequence coding for an epitope comprising at least one tumoral epitope of a tumor antigen.

This invention also provides a polynucleotide containing at least a part of the preS2 sequence of the genome of HBV, in which is inserted a DNA sequence coding for an epitope comprising at least one tumor epitope of a tumor antigen; and a nucleotidic sequence coding for the surface antigen of HBV. The epitope can comprise 1 to 30 epitopes, identical or different, and in a wild type or in a mutated configuration.

This invention also provides a composition containing the polynucleotide sequence of the invention for inducing in vivo an immune response against tumor specific antigens or tissue specific antigens.

This invention also provides a vector for induction of an in vivo cellular or humoral immune response using the polynucleotide of the invention and an early CMV promoter, preS2 and S nucleotide sequences encoding preS2 and S antigens of HBV; nucleotide sequences derived from the genome of HBV containing postranscriptional regulatory elements (PRE) and allowing nuclear export of RNA corresponding to nt 1151 to nucleotide 1684 of the HBV genome; and signal sequences for polyadenylation of messenger RNAs of HBV located at position nt 1921 to nt 1955 of the HBV genome; and nucleotide sequences of tumor epitopes surrounded up and down by alanine spacers. The vector can also have nucleotide sequences encoding a B cell epitope, which allows the detection of the hybrid proteins, said B cell epitope sequence being fused to the tumor sequences.

In addition, this invention provides a process of in vivo treatment, characterized by construction of a recombinant or synthetic polynucleotide sequence according to the invention; injection of the composition according to the invention to a host; and evaluation of cytotoxic response in host lymphocyte population.

Further, this invention provides a composition comprising a hybrid preS2-S protein containing tumor antigens (or epitope) capable of inducing, in vivo, a CTL response against several epitopes of one or more tumor antigens. The hybrid proteins in the composition can also contain a tag B cell epitope.

Further, this invention provides a recombinant particle comprising this composition and the small envelope protein of HBV.

Further, this invention provides a process of treatment cells of a host characterized by contacting the recombinant particles of the invention with the host's cells, and reinjection of treated cells into the host.

The PRE sequences are published in J. Virology 1996, pp. 4345-4351 (Donello el al.), the entire disclosure of which is relied upon and incorporated by reference herein. The cell epitope has a minimum of 5 amino acids. The CTL epitope has a minimum of 9 amino acids. The T helper epitope has a minium of 12 amino acids.

BRIEF DESCRIPTION OF THE DRAWINGS

This invention will be described in detail with reference to the drawings in which:

FIG. 1: Representation of the pCMV-B10 constructs and CTL responses of HHD mice injected with pCMV-B10 recombinant DNA coding a melanoma-based polyepitope.

A. Monoepitopic Constructs. The pCMV-B10 vector is a pcDNA3 derivative (INVITROGEN, Costa Mesa, Calif.) in which the largely overlapping coding and totally overlapping 3' untranslated nucleotide sequences for hepatitis B virus middle (and, initiation at ATG 900, termination at TAA 1744) and small (initiation at ATG 1066, termination at TAA 1744) envelope proteins have been inserted downstream of a human CMV immediate early promotor ($P_{CMV}$). The central part of the coding sequence for the preS2 segment was replaced by a polylinker and the coding sequence for a HIV 1-derived (MN isolate) V3 loop tag. The EcoRI and XhoI restriction sites were used to insert oligoniucleotides coding for the selected epitopes.

Amino acid sequence of the modified preS2 segment: MQWNSAAA[epitope]AAA LEHIGPGRAFVVPLEE-AWDPSRIGPANM (SEQ ID NO:1). The residual preS2 residues are in bold characters and the V3 loop tag residues in italics. The shaded area corresponds to the introduced epitopic peptide with alanine spacers, other residues originate from the residual polylinker nucleoticles except the C terminal methionine, which corresponds to position 1 of the hepatitis B virus small envelope protein.

B. Amino-acid sequence of the melanoma polyepitope (SEQ ID NO: 24).

C. CTL responses against HHD-transfected RMAS cells. Spleen cells of immunized mice were restimulated in vitro as indicated in the legend of Table 4. On day 6, cells were assayed against targets loaded with relevant (i.e., (NA17-A.nt38); MelanA/MART-1.27; gp100.154; gp100.457; Tyrosinase.368-D) and control inf.m.58 peptides. No specific lysis was obtained for MAGE-3.271, Tyrosinase.1, gp100.209, gp100.280, Melan-A/MART-1.32 epitopic peptides.

D. CTL responses against HHD-transfected HeLa target cells producing endogeneously the mnelanoma polyepitope.

Figure 2B:
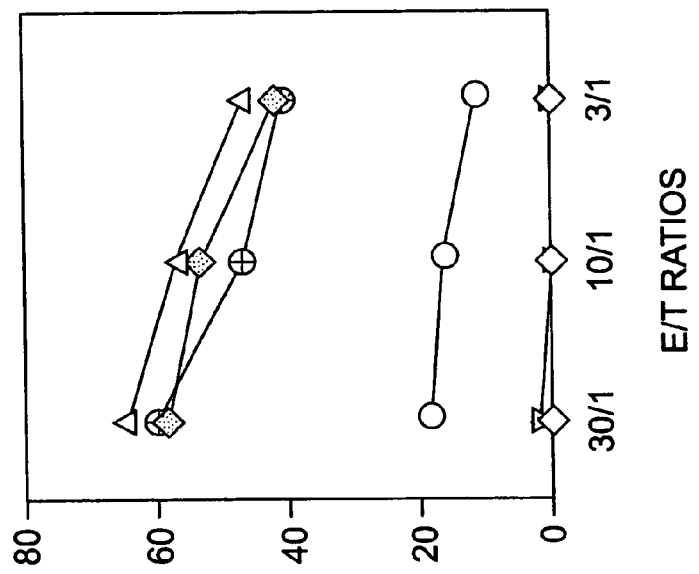
Figure 2A:
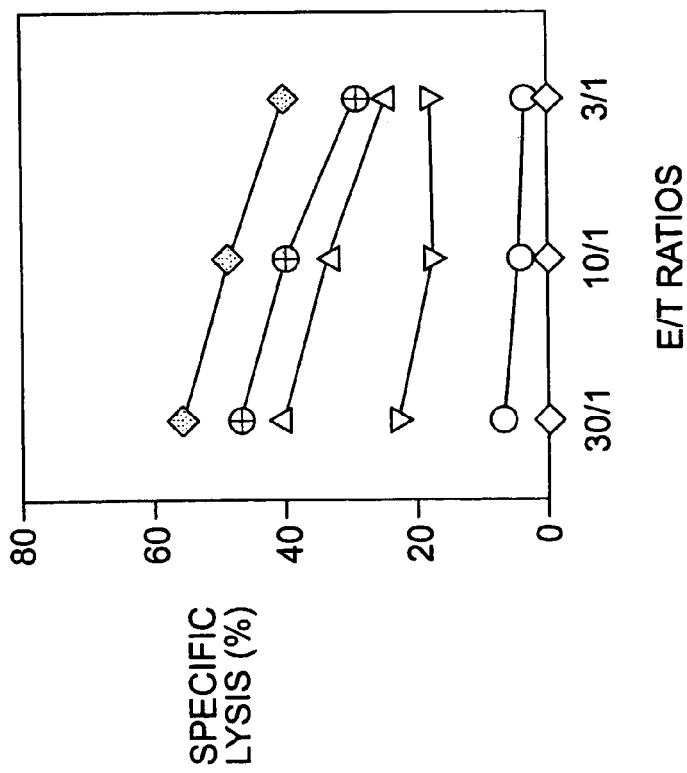

FIG. 2 is a graph, in two parts, depicting percents specific lysis vs. E/T ratios.

Figure 3:
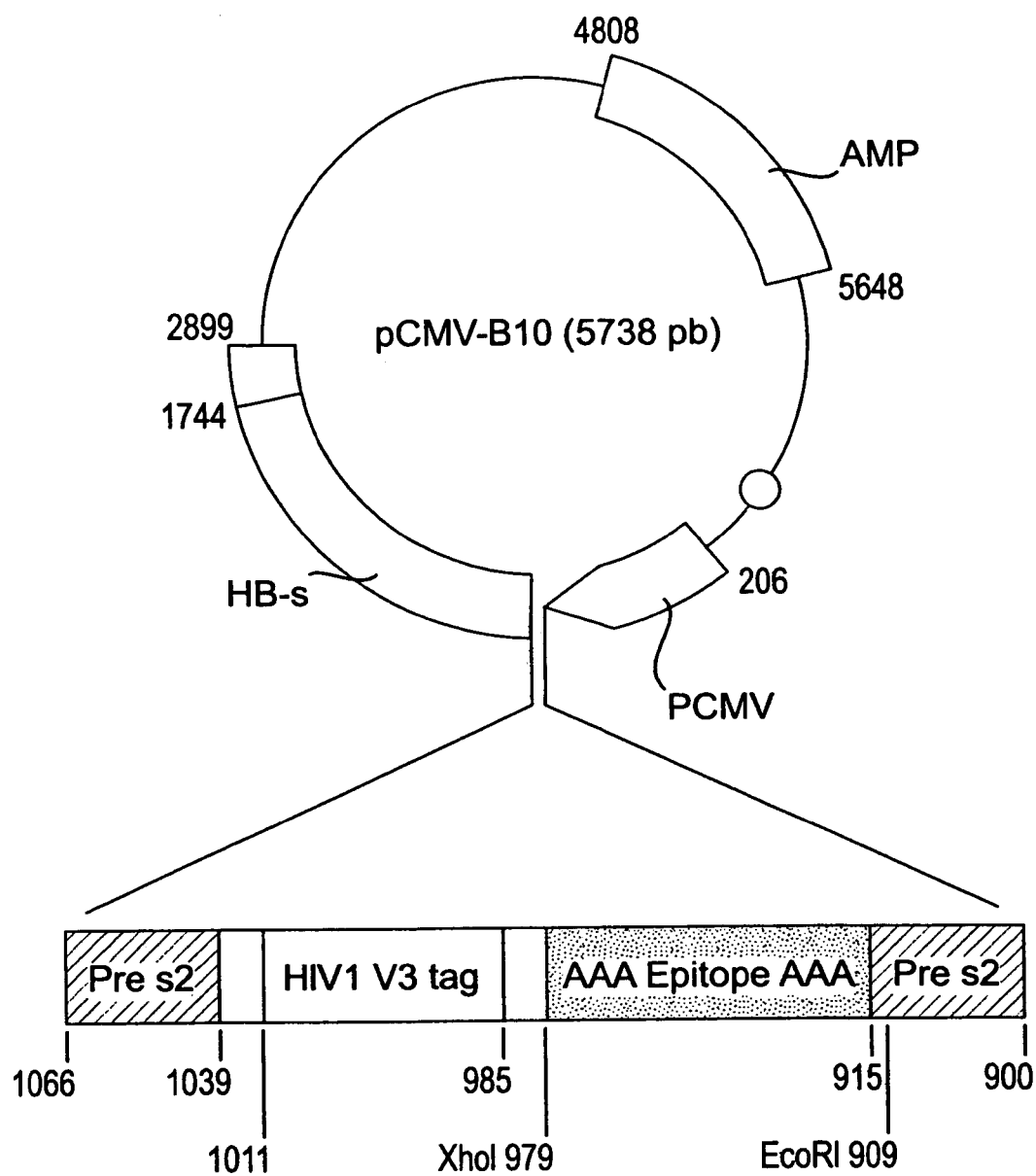

FIG. 3 is a plasmid map of plasmid pCMV-B10, which is useful in this invention.

DETAILED DESCRIPTION OF THE INVENTION

In one embodiment, this invention is related to the construction of a recombinant DNA containing 10 melanoma epitopcs inserted in a plasmid (pCMV-B10), which expressed also the pre-S2 and HIBS Ag. More generally, the invention relates to new recombinant HBS particles and nucleotidic sequences useful for the in vivo antitumoral therapy, immunization against tumoral antigens with a nucleotidic sequence or a vector encoding tumor epitopes and preS or preS2-S or S antigen of HBV. TIhe invention relates also to the new particles comprising S antigen of HBV preS2-S and tumoral peptides (or antigens tumoral).

The immunization of mice with this naked DNA elicited a very good CTL response against the melanoma polyepitope. The plasmid pCMV-B10 (FIG. 3) is derived from the plasmid pCMVHB-S2-S (CNCMI-1410) described in the PCT/FR 9400483 (WO 95-11307) corresponding to U.S. application Ser. No. 633,821 filed on Apr. 27, 1994, the entire disclosures of which are relied upon and incorporated by reference herein.

The HIV1-V3 Loop inserted between nt 1011 and nt 985 is used as a marker of expression. An insert of particular interest (in case of melanoma) is located at the XhoI site (nt 979) and no 915 as shown in FIG. 1. The HIV1-V3 loop can be replaced by any B cell epitope, which can be visualized. The size of the insert in this plasmid is very flexible.

The polyepitope has been published by Firat et al. in Eur. Journal of Immunology, 1999, 29:1-6, the entire disclosure of which is relied upon and incorporated by reference herein, but the expression is obtained in a recombinant poxvirus vaccine, and the poxvaccine vectors are less safe than pre S2-S HBV particles. (Described in U.S. Pat. Nos. 5,314,808 and 5,591,638). A construction with the vector pCMV-S2-S and V3 loop of gp120 of HIV-1 has been published in 1998 (Virology, 1998, 240:304-315), the entire disclosure of which is relied upon and incorporated by reference herein. The details for the construction of pCMV-B10 are disclosed in the claims herein. Also relevant to the invention is the hepatitis B virus post transcriptional regulatory element composed of two sub-elements described in J. Virol. 70:4345-4351 (July 1996), tile entire disclosure of which is relied upon and incorporated by reference herein.

The possibility to introduce, without real size limitations, DNA inserts in the preS2 segment of the middle hepatitis B glycoprotein coding sequence will be exploited to further insert epitopes presented by other HLA class I alleles.

The two first selected (HLA-A3.1, Embo. J. 1984, 3:887-894, and H.A.-B7.2, PNAS, 1990, 87:2833-2837) should result in polyepitopes of vaccinal interest for more than 80% of the Caucasian human population.

More particularly, the inventors used H-2 class I negative HLA-A2.1 transgenic HHD mice to evaluate the immunogenic potential of 19 human tumor-associated CTL epitopes and to compare different immunization strategies. A parallel study of the CTL responses of H-2 positive A2A2$K^b$ classical transgenic mice illustrated the improved capacity of HHD transgenic mice to develop H.A.-A2.1-restricted CTL responses. This advantage was previously documented by analyzing antiviral responses (8) but could have resulted from the preferential development in classical transgenic mice of H-2-restricted CTL responses against other viral epitopes. This explanation cannot apply to the responses induced by H.A.-A2.1-restricted synthetic peptides. The present results suggest that the size of the H.A.-A2.1-educated $CD8^+$ peripheral T cell repertoire is larger in HHD than in A2A2$K^b$ transgenic mice, in spite of a 10-fold lower cell surface expression of the transgenic HHD molecules and 5-fold lower $CD8^+$ T cell number in the periphery (data not shown). The HHD and A2A2$K^b$ molecules being functionally equivalent in terms of antigen presentation (8), we have to postulate that in classical transgenic mice, the co-expression of the A2A2 $K^b$ and H-2 class I molecules at the thymic level results in preferential H-2-education. This could be due to the fact, documented for HLA-A2.1 molecules, that residues in the second domain of the heavy chain and some of β2m, participate in the CD8 accessory interaction (23). Assuming the affinity of the mouse CD8 molecules to remain higher for H-2 than for chimeric A2A2$K^b$ class I molecules, and the thymic education to be a saturable process, one can conceive tile quantitative advantage, in terms of HLA education, that would result from the absence of H-2 class I molecules.

Immunizing HHD mice with human tumor-derived CD8 epitopic particles alone in IFA, lead us to devise a hierarchy which correlates, although imperfectly, with their binding and stabilizing capacities of HLA-A2.1 molecules. One might wonder whether this hierarchy also applies to humans. It appears unlikely that TcR differences between human and mouse could be of any significant influence considering the huge diversity of the T cell repertoire in both species and the absence of species-specific structural features in the variable TcR segments (24). Self-tolerance and accumulated phylogenic protein differences are more likely to modulate in a species specific manner this epitopic hierarchy. However, the human genetic polymorphism should also, to some extent, have the same consequences at the individual level. Using antigenic formulations which need to be processed, such as Ty-VLP and recombinant HBs particles, one should finally consider the possibility that the cell processing machinery of mouse and man could be functionally different. One such difference concerns the TAP pumps, the human one transporting more efficiently than its mouse counterpart peptides with positively charged C-terminal residues (25). This is of no relevance for H.A.-A2.1 transgenic mice, since this molecule binds peptides with leucine or methioninie C-termini which are efficiently transported by the mouse TAP pump (26). In fact, so far, all reported observations, except those concerning TAP, suggest a large functional redundancy between the mouse and human processing imachineries (6, 27).

The potent CTL responses induced either by Ty-VLP or recombinant pCMV-B10 (HBs) DNA were anticipated. Particulate antigens, which should also be released in the organism after intramuscular injection of the recombinant HBs DNA, are good inmunogens (41). Endosomal processing of the p1 and HBs proteins included in these particulate antigens might also result in the production of helper peptides which facilitate the development of cytotoxic responses. Of special interest, was the possibility of simultaneously inducing, in a single mouse, CTL responses against 5 different peptides included in the melanoma-based polyepitopic construct. This should compensate for the differences in expression of the molecules of immunological interest among melanomas (9) and reduce the risk of tumor escape. Among the 5 epitopic peptides for which CTL responses were documented, three (gp100.154, NA17-A.nt38, and MelanA/MART-1.27) are of special interest since they are expressed in 40, 50, and 40% respectively, of melanomas, with the expression of the NA17-A.nt38 epitope restricted to malignant cells. The 5 epitopes which did not induce CTL responses after polyepitopic immunization are poor binders and poor stabilizers. Modifications are currently tested to enhance their binding and stabilizing capacities and HHD mice are used to verify that the CTL responses they induce cross-recognize the wild-type epitopes.

The weakness of the CTL responses induced by peptide-loaded dendritic cells generated in vitro, was unexpected. This strategy has been documented as very efficient in many situations (28, 29, 30). One explanation could be that HHD mice are not congenic. Minor histocompatibility antigen differences could result in rapid destruction of the injected cells by the recipient mice. Backcrosses are underway to reach a B6 homogeneous genetic background and evaluate such a possibility. Such B6 congenic HHD mice would also provide us with the possibility to evaluate, using EL4 β2m negative HHD$^+$ S3$^-$Rob transfectants (8), the protection conferred by the elicited CTL responses.

EXAMPLES

This invention will be described in greater detail in the following examples, which are exemplary only, and do not in any way limit the scope of the invention.

Materials and Methods

Mice

HHD mice express a transgenic monochain histocompatibility class I molecule in which the C terminus of the human β2m is covalently linked to the N terminus of a chimeric heavy chain (HLA-A2.1 α1-α2, H-2D$^b$ α3-transmembrane, and intracytoplasmic domains). The H-2D$^b$ and mouse β2m genes of these mice have been disrupted by homologous recombination resulting in complete lack of serologically detectable cell surface expression of mouse histocompatibility class I molecules. A2A2K$^b$ mice were obtained from HARLAN SPRAGUE DAWLEY (Indianapolis, Ind.). These mice express chimeric heavy chain (HLA-A2.1 α1α2, H-2k$^b$ α3 transmembrane, and cytoplasmic domains) in non-covalent association with mouse β2m. They additionally express a full set of C57BI/6 derived (H-2$^b$) class 1a and 1b mouse histocompatibility molecules. All mice used were bred in our animal facility.

Peptides, Lipopeptides and Immunization Procedures

Peptides, purchased from either NEOSYSTEM (Strasbourg, France) or SYNT:EM (Nimes, France), were dissolved in dimethylsulfoxide (DMSO, 20 μl/mg of peptide) and subsequently diluted in PBS 1× (2 mg/ml). Mice were injected subcutaneously at the base of the tail with 100 μg of a H.A.-A2.1-restricted peptide, with or without 140 μg of the helper peptide, emulsified (v/v) in IFA (DIFCO, Detroit, Mich.) 7 days before in vitro re-stimulation. Lipopeptides were synthesized as already described (21) resulting in covalent linkage of the peptide N terminus to a S-[2.3 palmitoyloxy-(2-R)-propyl]-N-palmitoyl-(R)-Cysteine moiety (P3C) via a two serine spacer. Lipopeptides were dissolved in DMSO (20 μl/mg), then diluted in PBS 1× (2 mg/ml). One hundred μg were injected i.p. 2 weeks before in vitro restimulation.

Recombinant HBs DNA Constructs and Immunization Procedure

Synthetic complementary oligonucleotides corresponding to the selected T cell epitopes were individually inserted into the pre-S2 segment of the hepatitis B surface (HBs) middle protein using a pCMV-B10 mammalian cell-expression vector (FIG. 1A) (20). Each epitope was flanked on both sides by a 3 alanine spacer. A HIV-1 derived V3 loop tag was inserted in the pre-S2 sequence just after the C-terminal alanine spacer. Recombinant plasmids were purified on LPS-free QIAGEN columns (QIAGEN, Hilden, Germany). Mice were injected i.m. with 10 μM cardiotoxin (LATOXAN, Rosans, France) in 50 μl PBS 1× and, 5 days later, with 50 μg of pCMV-B10 DNA for a 21 day priming.

Recombinant Ty-VLP and Immunization Procedure

Construction and purification of recombinant Ty-VLP were performed as previously described using a pOGS40 yeast-expression vector (31). PCR-amplified oligonucleotides corresponding to the selected epitopes were produced from the recombinant pCMV-B10 constructs, in order to include the two 3 alanine spacers and the HIV 1-derived V3 loop tag. They were introduced in frame in a BamHI site at the 3' end of the coding sequence of the Ty p1 protein. Ty-VLP and purification were monitored by western blotting using mAb F5.5 against the V3 loop tag (HYBRIDOLAB, Institut Pasteur, Paris, France). The hybrid Ty-VLPs were injected (100 μg/mouse) s.c. into mice for a 14 day in vivo immunization.

Polyepitopic Recombinant HBs DNA Construct

A DNA sequence encoding 10 melanoma-derived H.A.-A2.1-restricted CTL epitopes (FIG. 1B) was amplified by PCR (Mateo L, in preparation). The polyepitope sequence was inserted in frame between the EcoRI-XhoI sites of the pCMV-B10 expression vector. Immunizations with naked DNA and in vitro restimulations were performed as described above, except that 10% TCGF was added to the culture medium for the last two days of culture.

Generation of Dendritic Cells and Immunization Procedure

Bone marrow-derived dendritic cells were obtained as previously described (32) with some modifications. Bone marrow mononuclear cells were cultured in RPMI supplemented with 10% FCS, 2 mM L glutamine, 50 U/ml penicillin, 50 µg/ml streptomycin, and 2-mercaptoethanol (complete RPMI medium), further supplemented with 20 ng/ml of recombinant mouse GM-CSF and 100 ng/ml recombinant mouse IL4 (both from GENZYME, Cambridge, Mass.). On days 2 and 6, non-adherent cells were removed, and fresh complete RPMI medium, supplemented with 10 ng/ml mouse GM-CSF and 50 ng Mouse IL4, was added. On day 7, the culture medium was replaced by complete RPMI medium supplemented with 100 U/ml of mouse TNFα. Dendritic cells, collected on day 9, were more than 95% pure (IA$^{b+}$, HHD$^+$, CD3$^-$, 33D1$^+$, NDL145$^+$, and CD 11c$^+$) as assessed with appropriate mAb. Those dendritic cells were loaded with peptides (2×10$^6$ cells/ml, 10 µg/ml of peptides, 2 h at RT in FCS-free RPMI medium), then washed (×3) and injected (1×10$^6$ cells/mouse) i.v. into recipient mice for in vivo priming 14 days before in vitro restimulation.

In vitro Restimulation and Cytolytic Assays

Spleen cells from primed mice were restimulated using irradiated (5000 rads) peptide-loaded (5.10$^6$ cells/ml, 10 µg/ml peptide, 2 h at RT in FCS-free RPMI medium), LPS-induced (25 µg/ml LPS, 7 µg/ml dextran sulfate, in complete RPMI medium, 48 h of culture) HHD lymphoblasts. On day 6, cultured cells were tested in a 4 h $^{51}$Cr-release assay, using as targets HHD-transfected TAP$^-$ RMA-S cells loaded with relevant or negative control influenza matrix 58-66 (Inf.m.58) peptides (10 µg/ml, 5.10$^6$ cells/ml, in FCS-free RPMI medium, 2 h at RT). Specific lysis was calculated as follows:

(experimental release–spontaneous release)/total release–spontaneous release)×100.

Peptide Binding and Stabilization of H.A.-A2.1 Molecules

T2 (TAP$^-$, H.A.-A2.1) cells were incubated overnight at 37° C. (1×10$^6$ cells/ml) in FCS-free RPMI medium supplemented with 100 ng/ml of human β2m (SIGMA, St Louis, Mo.) in the absence (negative control) or presence of either reference HIV 1 reverse transcriptase 476-484 (HIV 1 rt.476) or tested peptides at various final concentrations (100, 10, 1, and 0.1 µM). Following a 1 h incubation with brefeldine A (0.5 µg/ml, SIGMA), T2 Cells were labeled (30 min, 4° C.) with a saturating concentration of anti-H.A.-A2.1 (BB7.2) mAb, then washed twice. The cells were then incubated (30 min, 4° C.) with saturating concentration of FITC-conjugated goat IgG F(ab')2 anti-mouse Ig (CALTAG, South San Francisco, Calif.), washed (×2), fixed in PBS 1×, 1% paraformaldehyde and analyzed using a FACs Calibur cytofluorometer (BECTON DICKINSON, IMMUNOCYTOMETRY SYSTEMS, San Jose, Calif.). The mean intensity of fluorescence (MIF), observed for each peptide concentration (after subtraction of the MIF observed without peptide), was used as an estimate of peptide binding. For each peptide, the concentration needed to reach 20% of the maximal binding (as defined with HIV 1 rt.476 peptide) was calculated. Relative affinity (RA) is the ratio of the concentrations of tested and HIV 1 rt.476 reference peptides needed to reach this value. The lower the RA, the stronger the binding. Stabilization assays were performed similarly. Following initial evaluation of peptide binding (t 0), cells were washed in RPml complete medium to remove free peptides and incubated, in the continuous presence of brefeldine A (0.5 µg/ml) for 2, 4, 6, and 8 h. The amount of stable peptide-HLA-A2.1 complexes was estimated, as described above, by indirect immunofluorescence analysis. The half-life of complexes (DC50) is the time required for a 50% reduction of the to MIF value.

Example 1

Comparative Evaluation of the Immunogenic Potential of Human Tumor-Derived CD8 Epitopic Peptides with HHD and A2A2 K$^b$ Mice Nineteen HLA-A2.1 restricted synthetic epitopic peptides (9, 10, 11, 12) listed in Table 1 were injected s.c. in IFA in at least six H-2 negative HHD mice and six H-2 positive, A2A2K$^b$ transgenic mice. Seven days later, spleen cells from each animal were separately restimulated in vitro and then tested against Transporter associated with Antigen Presentation (TAP)-deficient HHD-transfected RMA-S peptide-loaded target cells.

Only 3 peptides elicited H.A.-A2.1-restricted CTL responses in A2A2 K$^b$ mice whereas 12 did so in HHD mice (Table 2). Considering the number of responding mice and the level of specific lysis, a hierarchy could be devised with strong (gp100.154 and CEA.571), intermediate (Tyrosinase.368-N, NA17-A.nt38, p53.65, and Her2/neu.369), weak (gpI00.209, gp100.280, gp100.476, Melan-A/MART-1.27, Tyrosinase.368-D, MAGE-3.271, and Her2/neu.654), and inefficient (gp100.457, Melan-A/MART-1.32, Tyrosinase.1, p53.149, p53.264, and HPV E7.86) CTL inducers.

TABLE 1

List of the epitopic peptides tested[a]

| Protein | Epitopic peptide | Sequence |
|---|---|---|
| Human melanoma | | |
| gp100 | 154-162 | KTWGQYWQV (SEQ ID NO:2) |
| | 209-217 | ITDQVPFSV (SEQ ID NO:3) |
| | 280-288 | YLEPGPVTA (SEQ ID NO:4) |
| | 457-466 | LLDGTATLRL (SEQ ID NO:5) |
| | 476-485 | VLYRYGSFSV (SEQ ID NO:6) |
| Melan-A/ | 27-35 | AAGIGILTV (SEQ ID NO:7) |
| MART-1 | 32-40 | ILTVILGVL (SEQ ID NO:8) |
| Tyrosinase | 1-9 | MLLAVLYCL (SEQ ID NO:9) |
| | 368-376-D[b] | YMDGTMSQV (SEQ ID NO:10) |
| | 368-376-N[b] | YMNGTMSOV (SEQ ID NO:11) |
| NA17-A | nt38-64[c] | VLPDVFIRC (SEQ ID NO:12) |
| MAGE-3 | 271-279 | FLWGPRALV (SEQ ID NO:13) |
| other human tumors | | |
| CEA | 571-579 | YLSGANLNL (SEQ ID NO:14) |
| p53 | 65-73 | RMPEAAPPV (SEQ ID NO:15) |
| | 149-157 | STPPPGTRV (SEQ ID NO:16) |
| | 264-272 | LLGRNSFEV (SEQ ID NO:17) |
| Her2/neu | 369-377 | XIFGSLAFL (SEQ ID NO:18) |
| | 654-662 | IISAVVGIL (SEQ ID NO:19) |
| HPV16 E7 | 86-93 | TLGIVCPI (SEQ ID NO:20) |

TABLE 1-continued

List of the epitopic peptides tested[a]

| Protein | Epitopic peptide | Sequence |
|---|---|---|
| Viruses | | |
| Inf. m | 58-66 | GILGFVFTL (SEQ ID NO:21) |
| HBVc | 128-140 | TPPAYRPPNAPIL (SEQ ID NO:22) |
| HIV 1 rt | 476-484 | ILKEPVHGV (SEQ ID NO:23) |

[a]Human melanoma and other tumor epitopic peptides have been reviewed recently (9). Influenza matrix (Inf.m.58), hepatitis B virus core (HBVc) and HIV 1 reverse transcriptase (rt) epitopic peptides are from references 10-12 respectively.
[b]Asparagine 370 being a glycosylation site, cytosolic deglycosylation results in presentation to CTL of the 368-376 epitopic peplicle with a Aspartate 370 residue.
[c]Epitopic peptide corresponding to a tumor-specific transcript initiated by a cryptic promotor and resulting in the translation of intronic nucleotides (38 to 64) of the N-Acetyl glucosaminyl-Transferase-V gene.

Example 2

HLA-A2.1 Binding and Stabilizing Capacities of the Epitopic Peptides

The immunogenicity of CD8 epitopic peptides largely reflects their binding and stabilizing capacities, with most of the strong CTL-inducers being both good binders and stabilizers (13, 14). Using TAP-deficient, H.A.-A2.1+ T2 cells, we evaluated these parameters in an immunofluorescence assay as indicated in Materials and Methods section.

The results shown in Table 2 demonstrate that as a rule, strong and intermediate CTL-inducers fell into the strong binder, strong stabilizer group (RA<3, DC50>4 h). There were, however, exceptions, most of which concern peptides such as MAGE-3.271, and p53.264 with high binding and stabilizing capacities, but poor CTL-induction capacity. Thus, H.A.-A2.1 binding and stabilizing capacities of epitopic peptides correlate well, but not completely, with peptide immunogenicity.

TABLE 2

CTL responses against tumor epitopic peptides in IFA and H.A.-A2.1 peptide binding and stabilizing capacities.

| Peptide | HHD mice[a] R/T (lysis in %)[b] | | A2A2Kb mice[a] R/T (lysis in %)[b] | | RA[c] | D50(h)[d] |
|---|---|---|---|---|---|---|
| gp100.154 | 4/6 | (39, 51, 57, 60) | 5/6 | (22, 34, 39, 44, 50) | 2.28 | 6-8 |
| gp100.209 | 1/6 | (23) | 0/6 | | 1.32 | 4 |
| gp100.280 | 3/16 | (13, 23, 47) | 0/6 | | 1.35 | 4 |
| gp100.457 | 0/6 | | 0/6 | | 1.65 | 2-4 |
| gp100.476 | 2/6 | (54, 70) | 1/6 | (29) | 10 | 4-6 |
| Melan-A/MART-1.27 | 2/8 | (15, 19) | 0/6 | | 2.16 | 4 |
| Melan-A/MART-1.32 | 0/6 | | 0/6 | | 21.1 | 2-4 |
| Tyrosinase.1 | 0/10 | | 0/6 | | >60 | 2-4 |
| Tyrosinase.368-D | 1/6 | (10) | 0/6 | | 2.27 | >6 |
| Tyrosinase.368-N | 4/15 | (12, 12, 20, 29) | 0/6 | | 2.2 | >8 |
| NA17-A.nt38 | 4/7 | (15, 23, 25, 30) | 0/6 | | 1.52 | >8 |
| MAGE-3.271 | 1/6 | (33) | 0/6 | | 0.91 | 6 |
| CEA.57-1 | 6/6 | (64, 67, 70, 71, 73, 75) | 0/6 | | 2.8 | >8 |
| p.53.65 | 4/6 | (10, 12, 26, 60) | 0/6 | | 0.91 | 6-8 |
| p53.149 | 0/6 | | 0/6 | | 36.6 | <2 |
| p53.264 | 0/7 | | 0/6 | | 2.09 | 6-8 |
| Her2/neu.369 | 5/6 | (12, 18, 22, 33, 39) | 0/6 | | 2.24 | 6-8 |
| Her2/neu.654 | 1/6 | (42) | 0/6 | | 11 | 4 |
| HPV E7.88 | 0/6 | | 2/6 | (10, 13) | 0.9 | >8 |

[a]Spleen cells from mice injected s.c. with peptide In IFA 7 days before were in vitro restimulated and assayed 6 days later against HHD-transfected RMA-S cells loaded with relevant or control (inf.m.58) peptides.
[b]R/T: responder versus tested mice. Mice were considered as responders when at least 10% specific lysis was observed. The values in parenthesis correspond to the maximal lysis observed for each responder mouse, usually at a 60:1 E/T ratio.
[c]Relative affinity (RA) is the ratio of the concentrations of tested versus reference peptides needed to reach 20% of the maximal amount of stabilized molecules as defined with high concentrations of reference peptide.
[d]Half-life of stabilized peptide-HLA-A2.1 complexes (DC 50) was evaluated following T2 cells and peplicle overnight incubation by measuring the amount of residual cell surface peptide-HLA-A2.1 complexes at time intervals (0, 2, 4, 6, 8 h) using indirect immunofluorescence and FACS analysis.

Example 3

Co-Immunization with Helper Hepatitis B Virus Core (HBVc 128-140) Peptide

Whereas the sole immunization with class I-restricted synthetic peptides of optimal size is sufficient for the induction of CTL responses in some cases (15), the need for help has been documented in other circumstances (16). Therefore, the CTL responses of HHD mice which express H-2$^b$ class II molecules were tested by co-injecting tumor-associated peptides and the 1A$^{b-}$ restricted HBVc.128 peptide (11).

Globally, all cytolytic responses were either induced or improved, except in the case of the Her2/neu.654 peptide (Table 3). Peptides of the weak and inefficient CTL-inducer groups (gp100.457, Tyrosinase.1, and MAGE-3.271) elicited good CTL responses in a large proportion of mice when co-injected with the helper peptide and peptides of the strong or intermediate CTL-inducer group (gp100.154, NA17-A.nt38, p53.65 and Her2/neu.368) elicited stronger responses in a larger proportion of mice. However, one noticeable exception, the CEA.571 peptide, turned out to be less immunogenic when co-injected with the helper peptide.

TABLE 3

CTL responses of HHD mice co-immunized in IFA with HBVC.128 helper peptide[a]

| Peptide | R/T[b] | (lysis in %) |
|---|---|---|
| gp100.154 | 9/11 | (43, 59, 60, 64, 77. 77, 80, 82, 85) |
| gp100.209 | 3/6 | (31, 36, 56) |
| gp100.280 | 2/8 | (12, 16) |
| gp100.457 | 5/6 | (14, 35, 43, 77, 79) |
| gp100.476 | 6/7 | (20, 22, 59, 63, 75, 79) |
| Melan-A/MART-1.27 | 4/5 | (10, 19, 20, 30) |
| Melan-A/MART-1.32 | 1/6 | (10) |
| Tyrosinase.1 | 5/6 | (27, 33, 40, 42, 51) |
| Tyrosinase.368-N | 5/12 | (21, 36, 70, 72, 78) |
| Tyrosinase.368-D | 2/6 | (13, 15) |
| NA7-A.nt38 | 5/6 | (36, 39, 61,64, 71) |
| MAGE-3.271 | 6/6 | (34, 38, 59, 63, 64, 79) |
| CEA.571 | 3/6 | (20, 32, 46) |
| p53.65 | 5/6 | (29, 31, 40, 41, 55) |
| p53.149 | 3/6 | (20, 51, 71) |
| p53.264 | 2/3 | (37, 64) |
| Her2/neu.369 | 7/8 | (21, 23, 25, 39, 40, 72, 75) |
| Her2/neu.654 | 0/6 | |
| HPV 16 E7.86 | 2/6 | (34, 48) |

[a]Spleen cells from mice, co-injected s.c. with CD8 epitopic (50 μg) and helper (140 μg) peptides in IFA 7 days before, were in vitro restimulated with peptide-loaded LPS-lymphoblasts and assayed 6 days later at different E/T ratios against HHD-transfected RMA-S target cells loaded with relevant or control (Inf.m.58) peptides.
[b]R/T, responder versus tested mice (see table 2[b])

Example 4

Comparison of Monoepitopic Immunization Strategics

Five peptides, one strong (CEA.571), two intermediate (NA17-A.nt38, Tyrosinase.368-N), and two weak (gp100.280, Tyrosinase.368-D) CTL-inducers were selected for this study. Four immunization strategies were compared: peptide-loaded, in vitro generated dendritic cells (17, 18), yeast-derived hybrid Ty-virus like particles (VLP) (19), recombinant Hepatitis B surface (HBs) middle protein encoding DNA (pCMV-B10-DNA) (20) and lipopeptides (21). Following in vitro restimulation, spleen cells of HHD mice were individually tested in a CTL assay.

Immunization with recombinant Ty-VLP and recombinant pCMV-B10-DNA gave the best results with strong CTL responses against CEA.571, and NA17-A.nt38 T cell epitopes in all animals tested (Table 4). Some responses of weak to strong magnitude could even be elicited against the weak CTL-inducers gp100.280 and Tyrosinase.368-D. Immunization with lipopeptides resulted in CTL responses but with large inter-individual differences. Surprisingly, peptide-loaded dendritic cells (95% pure), gave poor results. It is noteworthy that the weak CTL responses observed in this latter case were clearly evidenced following a second in vitro restimulation in the presence of IL2.

TABLE 4

CTL responses against tumor epitopic peptides in IFA and H.A.-A2.1 peptide binding and stabilizing capacities.

| | Mice | gp100.280 lysis in % | Tyrosinase 368-D lysis in % | Tyrosinase 368-N lysis in % | NA17-A.nt38 lysis in % | CEA.571 lysis in % |
|---|---|---|---|---|---|---|
| Dendritic cells | 1 | 0 (0) | 7 (68) | 15 (61) | 6 (7) | 2 (0) |
| | 2 | 0 (0) | 23 (56) | 0 (1) | 0 (2) | 4 (22) |
| | 3 | 0 (1) | 12 (64) | 0 (3) | 0 (6) | 4 (1) |
| | 4 | 0 (0) | 20 (64) | 0 (17) | 3 (5) | 1 (5) |
| | 5 | 0 (1) | 8 (92) | 0 (30) | 5 (24) | 1 (2) |
| | 6 | 0 (1) | 3 (71) | 8 (80) | 3 (9) | 0 (0) |
| Ty-VLP | 1 | 8 | nd | 0 | 55 | 56 |
| | 2 | 3 | nd | 61 | 39 | 59 |
| | 3 | 1 | nd | 58 | 50 | 51 |
| | 4 | 8 | nd | 39 | 60 | 58 |
| | 5 | 4 | nd | 29 | 59 | 46 |
| | 6 | 18 | nd | 17 | 61 | 62 |
| pCMV-B10 DNA | 1 | 0 | 57 | 6 | 35 | 19 |
| | 2 | 0 | 55 | 12 | 43 | 66 |
| | 3 | 8 | 28 | 16 | 47 | 40 |
| | 4 | 36 | 58 | 13 | 44 | 65 |
| | 5 | 21 | 56 | 11 | 40 | 62 |
| | 6 | 9 | 28 | 38 | 54 | 55 |
| Lipopeptides | 1 | 0 | 0 | 51 | 0 | 0 |
| | 2 | 8 | 10 | 20 | 12 | 8 |
| | 3 | 40 | 1 | 0 | 0 | 8 |
| | 4 | 8 | 4 | 5 | 68 | 34 |
| | 5 | 0 | 0 | 11 | 65 | 3 |
| | 6 | 21 | 0 | 12 | 47 | 0 |

Spleen cells from mice previously injected with either peptide-loaded dendritic cells differentiated in vitro, on purified TY-VLP, on naked pCMV-B10 DNA encoding recombinant HBs particles, or lipopeptides were restimulated in vitro using peptide-loaded, irradiated LPS-lymphoblasts. Six days later, they were assayed at different E/T ratios against HHD-transfected RMAS cells loaded with relevant or control (Inf.m.58) peptides. The values correspond to the highest specific lysis observed, usually at a 60/1 E/T ratio. ND : not done. Numbers in parentheses: specific lysis following a second in vitro restimulation of effector cells in the presence of 10% TCGF.

Example 5

Melanoma Polycpitopic Immunization

Using a polyepitope construct (22), we evaluated the possibility of simultaneously inducing in a single mouse CTL responses against several melanoma epitopes. Six HHD mice were injected with pCMV-B10 DNA encoding recombinant preS2/S glycoproteins containing a polyepitopic melanoma-derived motif (FIGS. 1A and B). Following separate in vitro splenocyte restimulation by each epitopic peptide, they were individually assayed against peptide-loaded HHD-transfected RMA-S cells and HHD-transfected human HeLa cells further transfected with a HIV-1 derived polyepitope expression vector (H. Firat, in preparation).

Whether peptide-loaded cells or cells endogenously expressing the polyepitopic construct were used as target, specific CTL responses were regularly induced against 4 to 5 out of the 10 melanoma epitopes included in the polyepitopic motif (FIGS. 1C and D). Strong responses were elicited against gp100.154 and NA17-A.nt38 epitopic peptides classified as strong and intermediate CTIL-inducers, respectively. Significant responses were observed against gp100.457 and Melan-A/MART.1.27 (strong CTL-inducers when associated with a helper peptide). Tyrosinase.368-D or gp100.209 also elicited CTL responses depending on mice. The 4 epitopes (gp100.280, 100.476, Melan-A/MART.1,27, Melan-A/MART-1.32, and Tyrosinase.1) which did not elicit CTL responses all fall into the weak and non CTL-inducer groups when administered as synthetic peptide in IFA with or without helper peptide. In mice assayed 17 weeks after injection of the polyepitope, 4 out of the 5 CTL responses could still be documented (data not shown). This suggests that memory CTL can be elicited using pCMV-B10 DNA polyepitope immunization.

Abbreviations used: $\beta$2m, $\beta$2-microglobulin; DC50, Decay complexes 50 (half-life of peptide-HLA-A2.1 complexes); HBs middle protein, Hepatitis B surface middle protein; RA, relative affinity; TAP, Transporter associated with Antigen Presentation; VLP, virus-like particles.

REFERENCES

The entire disclosure of each of the following references is relied upon and incorporated by reference herein.

1. Melief, C. J., Tumor eradication by adoptive transfer of cytotoxic T lymphocytes. *Adv. Cancer Res.* 1992. 58: 143-175.

2. van der Bruggen, P., Traversari, C., Chomez, P., Lurquin, C., DePlaen, E., VandenEynde, B., Knuth, A. and Boon, T., A gene encoding an antigen recognized by cytolytic T lymphocytes on a human melanoma. *Science* 1991. 254: 1643-1647.

3. Rosenberg, S. A., Yang, J. C., Schwartzentruber, D. J., Hwu, P., Marincola, F. M., Topalian, S. L., Restifo, N. P., Dudley, M. E., Schwarz, S. L., Speiss, P. J., Wunderlich, J. R., Parkhurst, M. R., Kawakami, Y., Seipp, C. A., Einhorn, J. H. and White, D. E., Immunologic and therapeutic evaluation of a synthetic peptide vaccine for the treatment of patients with metastatic melanoma. *Nat. Med.* 1998. 4: 321-327.

4. Arnold, B. and Hämmerling, G. J., MHC class-1 transgenic mice. *Ann. Rev. Immunol.* 1991. 9: 297-322.

5. Kalinke, U., Arnold, B. and Hämmerling, G., Strong xenogeneic H.A. response in transgenic mice after introducting an α3 domain into H.A.-B27. *Nature* 1990. 348: 642-644.

6. Wentworth, P. A., Vitiello, A., Sidney, J., Keogh, E., Chesnut, R. W., Grey, H. and Sette, A., Differences and similarities in the A2.1-restricted cytotoxic T cell repertoire in humans and human leukocyte antigen-transgenic mice. *Eur. J. Immunol.* 1996. 26: 97-101.

7. Vitiello, A., Marchesinii, D., Furze, J., Sherman, L. A. and Chesnut, R. W., Analysis of the HLA-restricted infiuenza-specific cytotoxic T lymphocyte response in transgenic mice carrying a chimeric human-mouse class I Major Histocompatibility Complex. *J. Exp. Med.* 1991. 173:1007-1015.

8. Pascolo, S., Bervas, N., Ure, J. M., Smith, A. G., Lemonnier, F. A. and Pérarnau, B., H.A.-A2.1 -restricted education and cytolytic activity of CD8$^+$ T lymphocytes from $\beta$2 microglobulin ($\beta$2m) H.A.-A2.1 monochain tranisgenic H-2D$^b$ $\beta$2m double knockout mice. *J. Exp. Med.* 1997. 185: 2043-2051.

9. Kawakami, Y. and Rosenberg, S. A., Human tumor antigens recognized by T-cells. *Immnunol. Res.* 1997. 16: 313-339.

10. Tsomides, T. J., Walker, B. D. and Eisen, H. N., An optimal viral peptide recognized by CD8$^+$ T cells binds very tightly to the restricting class I major histocompatibility complex protein on intact cells but not to the purified class I protein. *Proc. Nati. Acad. Sci. USA* 1991. 88: 11276-11280.

11. Milich, D. R., Hughes, J. L., McLachlan, A., Thornton, G. B. and Moriarty, A., Hepatitis B synthetic immunogen comprised of nucleocapsid T-cell sites and an envelope B-cell epitope. *Proc. Natl. Acad. Sci. USA* 1988. 85: 1610-1614.

12. Bednarek, M. A., Sauma, S. Y., Gammon, M. C., Porter, G., Tamhankar, S., Williamson, A. R. and Zweerink, H. J., The minimum peptide epitope from the influenza virus matrix protein. Extra and intracellular loading of HLA-A2. *J. Immunol.* 1991. 147: 4047-4053.

13. Sette, A., Vitello, A., Reherman, B., Fowler, P., Nayersina, R., Kast, W. M., Melief, C. J., Oseroff, C., Yuan, L., Ruppert, J., The relationship between class I binding affinity and immunogenicity of potential cytotoxic T cell epitopes. *J. Immunol.* 1994. 153: 5586-5592.

14. van der Burg, S. H., Visseren, M. J., Brandt, R. M., Kast, W. M. and Melief, C. J., Immunogenicity of peptides bound to MHC class I molecules depends on the MHC-peptide complex stability. *J. Immunol.* 1996. 156: 3308-3314.

15. Vasilakos, J. P. and Michael, J. G., Herpes simplex virus class I-restricted peptide induces cytotoxic T lymphocytes in vivo independent of CD4+ T cells. *J. Immunol.* 1993. 150: 2346-2355.

16. Ossendorp, F., Mengede, E., Camps, M., Fillus, R. and Melief, C. J., Specific T helper cell requirement for optimal induction of cytotoxic T lymphocytes against major histocompatibility complex class II negative tumors. *J. Exp. Med.* 1998. 187: 693-702.

17. Huang, A. Y., Golumbek, P., Ahmadzadeh, M., Jaffee, E., Pardoll, D. and Levitsky, H., Role of bone marrow-derived cells in presenting MHC class I-restricted tumor antigens. *Science* 1994. 264: 961-965.

18. Mayordomo, J. I., Zorina, T., Storkus, W. J., Zitvogel, L., Celluzzi, C., Falo, L. D., Melief, C. J., Ildstad, S. T., Kast, W. M., Deleo, A. B., Bone marrow-derived dendritic cells pulsed with synthetic tumour peptides elicit protective and therapeutic antitumour immunity. *Nat. Med.* 1995. 1: 1297-1302.

19. Layton, G. T., Harris, S. J., Myhan, J., West, D., Gotch, F., Hill-Perkins, M., Cole, J. S., Meyers, N., Woodrow, S., French, T. J., Adams, S. E. and Kingsman, A. J., Induction of single and dual cytotoxic T-lymphocyte responses to viral proteins in mice using recombinant hybrid Ty-virus-like particles. *Immunology* 1996. 87: 171-178.

20. Le Borgne, S., Mancini, M., Le Grand, R., Schleef, M., Dormont, D., Tiollais, P., Riviere, Y. and Michel, M. L., In vivo induction of specific cytotoxic T lymphocytes in mice and rhesus macaques immunized with DNA vector encoding an HIV epitope fused with hepatitis B surface antigen. *Virology* 1998. 240: 304-315.

21. Deres, K., Schild, H., Wiesmuller, K. H., Jung, G. and Rammensee, H. G., In vivo priming of virus-specific cytotoxic T lymphocytes with synthetic lipopeptide vaccine. *Nature* 1989. 342: 561-564.

22. Thomson, S. A., Sherrit, M. A., Medveczky, J., Elliott, S. L., Moss, D. J., Fernando, G. J., Brown, L. E. and Suhrbier, A., Delivery of multiple CD8 cytotoxic T cell epitopes by DNA vaccination. *J. Immunol.* 1998. 160: 1717-1723.

23. Gao, G. F., Tormo, J., Gerth, U. C., Wyer, J. R., McMichael, A. J., Stuart, D. I., Bell, J. I., Jones, E. Y. and Jakobsen, B. K., Crystal structure of the complex between human CD8alpha(alpha) and HLA-A2. *Nature* 1997. 387: 630-634.

24. Wilson, R. K., Lai, E., Concannon, P., Barth, R. K. and Hood, L. E, Structure, organization and polymorphism of murine and human T-cell receptor alpha and beta chain gene families. *Immunol. Rev.* 1988. 101: 149-172.

25. Momburg, F., Roelse, J., Howard, J. C., Butcher, G. W., Hämmerling, G. J. and Neefles, J. J., Selectivity of MHC-encoded peptide transporters from human, mouse and rat. *Nature* 1994. 367: 648-651.

26. Falk, K., Röitzschke, O., Stevanovic, S., Jung, G. and Rammensee, H. G., Allele-specific motifs revealed by sequencing of self peptides eluted from MHC molecules. *Nature* 1991. 351: 290-296.

27. Shirai, M., Arichi, T., Nishioka, M., Nomura, T., Ikeda, K., Kawanishi, K., Engelhard, V. H., Feinstone, S. M. and Berzofsky, J. A., CTL responses of H.A.-A2.1-transgenic mice specific for hepatitis C viral peptides predict epitopes for CTL of humans carrying H.A.-A2.1. *J. Immunol.* 1995. 154: 2733-2742.

28. Song, W., Kong, H. L., Carpenter, H., Torii, H., Granstein, R., Rafii, S., Moore, M. A. and Crystal, R. G., Dendritic cells genetically modified with an adenovirus vector encoding the cDNA for a model antigen induce protective and therapeutic antitumor immunity. *J. Exp. Med.* 1997. 186: 1247-1256.

29. Specht, J. M., Wang, G., Do, M. T., Lam, J. S., Royal, R. E., Reeves, M. E., Rosenberg, S. A. and Hwu, P., Dendritic cells retrovirally transduced with a model antigen gene are therapeutically effective against established pulmonary metastases. *J. Exp. Med.* 1997. 186: 1213-1221.

30. Porgador, A., Snyder, D. and Gilboa, E., Induction of antitumor immunity using bone marrow-generated dendritic cells. *J. Immunol* 1996. 156: 2918-2926.

31. Burns, N. R., Gilmour, J. E., Kingsman, S. M., Kingsman, A. J. and Adams, S. E., Production and purification of hybrid Ty-VLPs. *Mol. Biotechnol.* 1994. 1: 137-145.

32. Inaba, K., Inaba, M., Deguchi, M., Hagi, K., Yasumizu, R., Ikehara, S., Muramatsu, S. and Steinman, R. M., Granulocytes, macrophages, and dendritic cells arise from a common major histocompatibility complex class II-negative progenitor in mouse bone marrow. *Proc. Natl. Acad. Sci. USA* 1993. 90: 3038-3042.

What is claimed is:

1. An isolated or purified polynucleotide comprising part of the preS2 sequence of HBV and a DNA sequence coding for at least one non-HBV epitope of a tumor antigen, which is inserted between the codon for amino acid 915 and the codon for amino acid 979 of the pre-S2 segment of the middle glycoprotein of the hepatitis B virus (HBV);

wherein the polynucleotide comprises a nucleotide sequence encoding hepatitis B virus surface antigen;

wherein the at least one non-HBV epitope of a tumor antigen is selected from AAGIGILTV (SEQ ID NO: 7), FLWGPRALV (SEQ ID NO: 13), MLLAVLYCL (SEQ ID NO: 9), LLDGTATLRL (SEQ ID NO: 5), KTWGQYWQV (SEQ ID NO: 2), YMDGTMSQV (SEQ ID NO: 10), ITDQVPFSV (SEQ ID NO: 3), YLEPGPVTA (SEQ ID NO: 4), ILTVILGV (SEQ ID NO: 8), YLPDVFIRC (SEQ ID NO: 12), gp100.154, gp100.209, gp100.280, gp100.457, gp100.476, Melan-A/MART-1.27, Melan-A/MART-1.32, Tyrosinase. 1, Tyrosinase.368-D, Tyrosinase.368-N, NA17-A.nt38, MAGE-3.271, CEA.57-1, p.53.65, p53.149, p53.264, Her2/neu.369, Her2/neu.654, and HPVE7.88; and wherein each epitope is flanked on each of its sides by three alanine amino acid residues and the preS2 sequence contains an HIV-1 V3 tag; and wherein injection of a synthetic peptide encoded by said polynucleotide into an H-2 negative HHD mouse elicits an H.A.-A2.1-restricted CTL response in the mouse, and the H.A.-A2.1-restricted CTL response is specific for the at least one epitope of a tumor antigen encoded by the DNA sequence.

2. The polynucleotide according to claim 1, wherein the inserted DNA sequence encodes a polyepitope up to 30 epitopes, wherein none, some, or all of the epitopes are the same.

3. The polynucleotide according to claim 2, wherein the polyepitope comprises up to 19 epitopes.

4. The polynucleotide according to claim 2, wherein the polyepitope comprises up to 10 epitopes.

5. The polynucleotide according to claim 2, wherein the polyepitope comprises up to 5 epitopes.

6. The polynucleotide according to claim 2, wherein the polyepitope comprises 5 to 19 epitopes.

7. The polynucleotide according to claim 2, wherein the polyepitope comprises 5 to 10 epitopes.

* * * * *

SEQUENCE LISTING

```
<160> NUMBER OF SEQ ID NOS: 25

<210> SEQ ID NO 1
<211> LENGTH: 8
<212> TYPE: PRT
<213> ORGANISM: Hepatitis B virus

<400> SEQUENCE: 1

Met Gln Trp Asn Ser Ala Ala Ala
  1               5

<210> SEQ ID NO 2
<211> LENGTH: 9
<212> TYPE: PRT
<213> ORGANISM: Homo sapiens

<400> SEQUENCE: 2

Lys Thr Trp Gly Gln Tyr Trp Gln Val
  1               5
```

```
<210> SEQ ID NO 3
<211> LENGTH: 9
<212> TYPE: PRT
<213> ORGANISM: Homo sapiens

<400> SEQUENCE: 3

Ile Thr Asp Gln Val Pro Phe Ser Val
 1               5

<210> SEQ ID NO 4
<211> LENGTH: 9
<212> TYPE: PRT
<213> ORGANISM: Homo sapiens

<400> SEQUENCE: 4

Tyr Leu Glu Pro Gly Pro Val Thr Ala
 1               5

<210> SEQ ID NO 5
<211> LENGTH: 10
<212> TYPE: PRT
<213> ORGANISM: Homo sapiens

<400> SEQUENCE: 5

Leu Leu Asp Gly Thr Ala Thr Leu Arg Leu
 1               5                   10

<210> SEQ ID NO 6
<211> LENGTH: 10
<212> TYPE: PRT
<213> ORGANISM: Homo sapiens

<400> SEQUENCE: 6

Val Leu Tyr Arg Tyr Gly Ser Phe Ser Val
 1               5                   10

<210> SEQ ID NO 7
<211> LENGTH: 9
<212> TYPE: PRT
<213> ORGANISM: Homo sapiens

<400> SEQUENCE: 7

Ala Ala Gly Ile Gly Ile Leu Thr Val
 1               5

<210> SEQ ID NO 8
<211> LENGTH: 9
<212> TYPE: PRT
<213> ORGANISM: Homo sapiens

<400> SEQUENCE: 8

Ile Leu Thr Val Ile Leu Gly Val Leu
 1               5

<210> SEQ ID NO 9
<211> LENGTH: 9
<212> TYPE: PRT
<213> ORGANISM: Homo sapiens

<400> SEQUENCE: 9

Met Leu Leu Ala Val Leu Tyr Cys Leu
 1               5

<210> SEQ ID NO 10
<211> LENGTH: 9
```

```
<212> TYPE: PRT
<213> ORGANISM: Homo sapiens

<400> SEQUENCE: 10

Tyr Met Asp Gly Thr Met Ser Gln Val
 1               5

<210> SEQ ID NO 11
<211> LENGTH: 8
<212> TYPE: PRT
<213> ORGANISM: Homo sapiens

<400> SEQUENCE: 11

Tyr Met Asn Gly Thr Met Ser Val
 1               5

<210> SEQ ID NO 12
<211> LENGTH: 9
<212> TYPE: PRT
<213> ORGANISM: Homo sapiens

<400> SEQUENCE: 12

Val Leu Pro Asp Val Phe Ile Arg Cys
 1               5

<210> SEQ ID NO 13
<211> LENGTH: 9
<212> TYPE: PRT
<213> ORGANISM: Homo sapiens

<400> SEQUENCE: 13

Phe Leu Trp Gly Pro Arg Ala Leu Val
 1               5

<210> SEQ ID NO 14
<211> LENGTH: 9
<212> TYPE: PRT
<213> ORGANISM: Homo sapiens

<400> SEQUENCE: 14

Tyr Leu Ser Gly Ala Asn Leu Asn Leu
 1               5

<210> SEQ ID NO 15
<211> LENGTH: 9
<212> TYPE: PRT
<213> ORGANISM: Homo sapiens

<400> SEQUENCE: 15

Arg Met Pro Glu Ala Ala Pro Pro Val
 1               5

<210> SEQ ID NO 16
<211> LENGTH: 9
<212> TYPE: PRT
<213> ORGANISM: Homo sapiens

<400> SEQUENCE: 16

Ser Thr Pro Pro Pro Gly Thr Arg Val
 1               5

<210> SEQ ID NO 17
<211> LENGTH: 9
<212> TYPE: PRT
<213> ORGANISM: Homo sapiens
```

```
<400> SEQUENCE: 17

Leu Leu Gly Arg Asn Ser Phe Glu Val
 1               5

<210> SEQ ID NO 18
<211> LENGTH: 9
<212> TYPE: PRT
<213> ORGANISM: Homo sapiens

<400> SEQUENCE: 18

Lys Ile Phe Gly Ser Leu Ala Phe Leu
 1               5

<210> SEQ ID NO 19
<211> LENGTH: 9
<212> TYPE: PRT
<213> ORGANISM: Homo sapiens

<400> SEQUENCE: 19

Ile Ile Ser Ala Val Val Gly Ile Leu
 1               5

<210> SEQ ID NO 20
<211> LENGTH: 8
<212> TYPE: PRT
<213> ORGANISM: Homo sapiens

<400> SEQUENCE: 20

Thr Leu Gly Ile Val Cys Pro Ile
 1               5

<210> SEQ ID NO 21
<211> LENGTH: 9
<212> TYPE: PRT
<213> ORGANISM: Influenza virus

<400> SEQUENCE: 21

Gly Ile Leu Gly Phe Val Phe Thr Leu
 1               5

<210> SEQ ID NO 22
<211> LENGTH: 13
<212> TYPE: PRT
<213> ORGANISM: Hepatitis B virus

<400> SEQUENCE: 22

Thr Pro Pro Ala Tyr Arg Pro Pro Asn Ala Pro Ile Leu
 1               5                  10

<210> SEQ ID NO 23
<211> LENGTH: 9
<212> TYPE: PRT
<213> ORGANISM: Human immunodeficiency virus type 1

<400> SEQUENCE: 23

Ile Leu Lys Glu Pro Val His Gly Val
 1               5

<210> SEQ ID NO 24
<211> LENGTH: 92
<212> TYPE: PRT
<213> ORGANISM: Artificial Sequence
<220> FEATURE:
<223> OTHER INFORMATION: Description of Artificial Sequence:  AMINO ACID
```

-continued

```
      SEQUENCE OF A MODIFIED PREX2 SEGMENT FROM
      HEPATITIS B VIRUS

<400> SEQUENCE: 24

Ala Ala Gly Ile Gly Ile Leu Thr Val Phe Leu Trp Gly Pro Arg Ala
  1               5                  10                  15

Leu Val Met Glu Leu Ala Val Leu Tyr Cys Leu Leu Leu Asp Gly Thr
             20                  25                  30

Ala Thr Leu Arg Leu Lys Thr Trp Gly Gln Tyr Trp Gln Val Tyr Met
         35                  40                  45

Asp Gly Thr Met Ser Asp Val Ile Thr Asp Gln Val Pro Phe Ser Val
     50                  55                  60

Tyr Leu Glu Phe Gly Pro Val Thr Ala Ile Leu Thr Val Ile Leu Gly
 65                  70                  75                  80

Val Leu Val Leu Pro Asp Val Phe Ile Arg Cys Val
                 85                  90

<210> SEQ ID NO 25
<211> LENGTH: 33
<212> TYPE: PRT
<213> ORGANISM: Hepatitis B virus

<400> SEQUENCE: 25

Ala Ala Ala Leu Glu His Ile Gly Pro Gly Arg Ala Phe Val Val Pro
  1               5                  10                  15

Leu Glu Glu Ala Trp Asp Pro Ser Arg Ile Gly Asp Pro Ala Leu Asn
             20                  25                  30

Met
```